United States Patent [19]

Hoffmann et al.

[11] 4,292,244
[45] Sep. 29, 1981

[54] NOVEL 2,4-DISUBSTITUTED PYRAN DERIVATIVES, THEIR PREPARATION AND THEIR USE AS SCENTS

[75] Inventors: Werner Hoffmann, Neuhofen; Frank Thoemel, Weinheim, both of Fed. Rep. of Germany

[73] Assignee: BASF Aktiengesellschaft, Fed. Rep. of Germany

[21] Appl. No.: 154,900

[22] Filed: May 30, 1980

[30] Foreign Application Priority Data

Jun. 21, 1979 [DE] Fed. Rep. of Germany ....... 2925043

[51] Int. Cl.$^3$ .................. C07D 309/20; C07D 309/24; C07D 309/26; C07D 309/22
[52] U.S. Cl. .......................... 260/345.1; 260/345.8 R; 260/345.9 R; 252/522 R
[58] Field of Search .................... 260/345.1, 345.8 R, 260/345.9 R

[56] References Cited

U.S. PATENT DOCUMENTS 3,309,276  3/1967  Cahn et al. .................. 260/345.1
4,070,491  1/1978  Vinals et al. ..................... 426/536
4,071,535  1/1978  Vinals et al. .................. 260/345.1

FOREIGN PATENT DOCUMENTS 1221388  2/1967  Fed. Rep. of Germany ... 260/345.1

OTHER PUBLICATIONS

Mühlstädt et al., Zeits. Chem., 11, 459 (1971).
Williams et al., Jacs, 72, 5738 (1950).
Hudson et al., Tetrahedron, 1957, vol. 1, pp. 284–288.
Derwent Pharmdoc 29159T-DE of Japanese Published Patent Application JA-PS 7214383, 2-13-70.
Amano et al., C. A. 77, 48243y and 48244z, (1972).
Patents Abstracts of Japan, vol. 1, No. 64, p. 889 C 77 (1977).

*Primary Examiner*—Nicky Chan
*Attorney, Agent, or Firm*—Keil & Witherspoon

[57] ABSTRACT

2-(1-methyl-eth-1-en-1-yl)-,2-(1-methyl-prop-1-en-1-yl)-, 2-(eth-1-en-1-yl)- and 2-(prop-1-en-1-yl)-4-methyl-2,3-dihydro-6H-pyrans substituted in the 2-position of the side chain by hydroxymethyl, acyloxymethyl, alkoxycarbonylmethyl, halomethyl or formyl. The novel 4-methyl-2,3-dihydro-6H-pyrans are obtained by reaction of 3-methyl-but-3-en-1-ol with an appropriately substituted unsaturated aldehyde in the presence of an acid catalyst. The products possess very interesting organoleptic properties.

1 Claim, No Drawings

NOVEL 2,4-DISUBSTITUTED PYRAN DERIVATIVES, THEIR PREPARATION AND THEIR USE AS SCENTS

The present invention relates to novel 2,4-disubstituted pyran derivatives of the general formula I

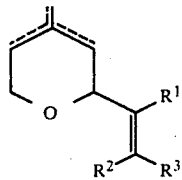
(I)

where $R^1$ and $R^2$ are each hydrogen or methyl and $R^3$ is —CH$_2$OH, —CH$_2$—O—COCH$_3$, —CH$_2$—OCHO, —CH$_2$—O—COC$_2$H$_5$, —COOCH$_3$, —COOC$_2$H$_5$, —COOC$_3$H$_7$, —CH$_2$Cl, —CH$_2$Br, —CH$_2$I or —CHO, and which possess a double bond within the region shown by the broken line, and to their use as scents.

Amongst the compounds of the pyran type occurring in nature, the compound referred to as rose oxide (IV) has acquired special importance because of its fragrance characteristics.

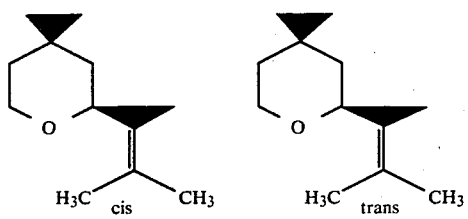
(IV)

Many attempts have therefore been made (cf., eg., Zeitschrift für Chemie 11 (1971), 459) to synthesize this component of Bulgarian attar of roses (in which about 1% of the (—)-cis-compound is present) and of the oil of Geranium bourbon (in which about 1% of (—)-cis-compound and (—)-trans-compound is present).

Certain purely synthetic compounds possessing rose fragrance or similar fragrance characteristics are derived from this naturally occurring prototype.

For example, German Pat. No. 1,221,388 discloses the condensation of 2-methyl-pentane-2,4-diol with mesityl oxide in the presence of sulfuric acid to give a pyran of the formula V

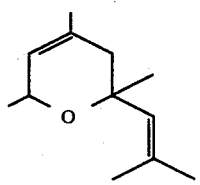
V which possesses a rose-like or geranium-like note.

This pyran was synthesized by a process which had been disclosed by Williams et al. (cf. J. Am. Chem. Soc., 72 (1950), 5738) for the condensation of aldehydes or ketones with 2-methyl-pentane-2,4-diol or 4-methyl-pent-4-en-2-ol, in the presence of acid catalysts, to give the corresponding pyran derivatives. Further information concerning the products obtained, and the mechanism of this cyclo-condensation reaction, were given in Tetrahedron 1 (1957), 284–88.

Further, U.S. Pat. Nos. 4,070,491 and 4,071,535 disclose that certain 2-alkyl-4-phenyl-dihydropyrans may be used to improve the organoleptic properties of foodstuffs and tobacco.

Japanese Published Patent Application 72/14,383 (Japanese Appln. 012,901) describes the oxidation of rose oxide to 2-(2-hydroxymethyl-prop-1-enyl)-4-methyltetrahydropyran VI, an aromatic having a mushroom-like note

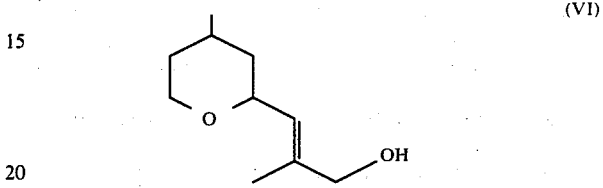
(VI)

We have found, surprisingly, that α,β-unsaturated aldehydes which in addition to the formyl group contain further functional groups, such as ester groups, a hydroxymethyl group, a formyl group or a halomethyl group in the β-position can also be cyclized, without particular difficulties and in good yields, with 3-methyl-but-3-en-1-ol in the presence of acid catalysts, to give the corresponding 2,4-disubstituted pyran derivatives, and that novel compounds with interesting fragrance notes are thereby formed.

Hence, the present invention also relates to a process for the preparation of the novel pyran derivatives of the general formula I, wherein 3-methyl-but-3-en-1-ol (II)

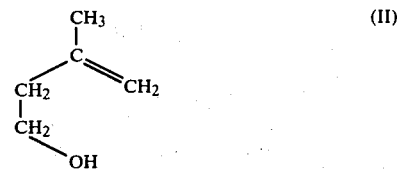
(II)

is reacted with an aldehyde of the general formula III

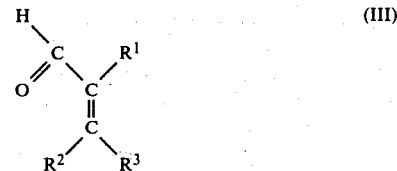
(III)

where $R^1$, $R^2$ and $R^3$ have the above meanings, in the presence of an acid catalyst.

To prepare the compound of the formula I, where $R^3$ is —CH$_2$OH, it is best to hydrolyze the corresponding acetate in a conventional manner or, more advantageously still, to subject it to a trans-esterification, for example with methanol in the presence of sodium methylate.

Examples of suitable α,β-unsaturated aldehydes of the general formula V, which contain further functional groups, are 2-methyl- and 3-methyl-4-acetoxy-but-2-en-1-al, methyl 3-formylcrotonate, ethyl 3-formylcrotonate, 2-methyl-4-chloro-but-2-en-1-al, 2-methyl-4-bromo-but-2-en-1-al and 4-acetoxy-but-2-en-1-al.

3-Methyl-but-3-en-1-ol (IV), required as the other reactant is a commercial compound which can be prepared from isobutylene and formaldehyde by a Prins reaction.

Suitable acid catalysts are strong inorganic acids, eg. $H_2SO_4$ and HCl, strong organic acids, eg. p-toluenesulfonic acid and oxalic acid, strongly acidic ion exchangers, and Brönstedt acids, eg. anhydrous $FeCl_3$ and $ZnCl_2$. The use of p-toluenesulfonic acid is particularly advantageous. The acid catalyst is in general used in an amount of from 0.1 millimole to 100 millimoles, preferably from 1 to 10 millimoles, per mole of 3-methyl-but-3-en-1-ol.

The reaction is in general carried out in a solvent, but it is also possible to work without a solvent, in which case, however, a larger amount of polymeric by-products is formed.

Examples of suitable solvents are methylene chloride, cyclohexane, toluene and hexane.

The reaction is in general carried out at from 50° to 150° C., preferably from 80° to 120° C. The reaction time is from 0.5 to 24 hours, preferably from 1 to 4 hours, depending on the reactant and on the reaction temperature.

The novel 2,4-disubstituted pyran derivatives possess very interesting organoleptic properties. They are fragrances with very interesting green notes and spicy, herbal or aromatic effects. The novel fragrances may be used for cosmetic preparations of all kinds, and for detergents and cleansers, and are also valuable fragrance improvers for industrial products. They may be used either in the pure form or as mixtures with other fragrances.

The process according to the invention provides a simple and economical method of obtaining the novel compounds.

EXAMPLE 1

43 g (0.5 mole) of 3-methyl-but-3-en-1-ol and 71 g (0.5 mole) of 2-methyl-4-acetoxy-but-2-en-1-al were dissolved in a mixture of 200 ml of toluene and 200 ml of hexane, 0.5 g of p-toluenesulfonic acid was added and the mixture was refluxed for 2 hours, during which 10.5 g of water were distilled off azeotropically. The reaction mixture was then washed neutral with water and the solvent was distilled off at 30° C. under 10 mbar. The residue was subjected to fractional distillation. This gave 81 g of a main fraction (77% of theory) which according to the NMR spectrum contained about 80% by weight of 2-(1-methyl-3-acetoxy-prop-1-en-1-yl)-4-methylenetetrahydropyran and about 10% by weight each of 2-(1-methyl-3-acetoxy-prop-1-en-1-yl)-4-methyl-5,6-dihydro-2H-pyran and 2-(1-methyl-3-acetoxy-prop-1-en-1-yl)-4-methyl-2,3-dihydro-6H-pyran. The boiling point of the mixture obtained was 75°–78° C./0.01 mbar; $n_D^{25} = 1.4890$; fragrance note: green, dill-like, cucumber haulms.

EXAMPLE 2

515 g (2.45 moles) of a pyran mixture obtained as described in Example 1 were dissolved in 416 g (13 moles) of methanol, 3 g of a 30% strength solution of sodium methylate in methanol was added, as a catalyst, to the solution, and the batch was refluxed. The methyl acetate formed in this trans-esterification reaction was distilled off continuously through a 50 cm column containing glass packings. After completion of the formation of methyl acetate, the excess methanol was distilled off and the reaction product was subjected to fractional distillation. This gave 392 g of a main fraction which according to the NMR spectrum corresponds, in its isomer composition, to the starting material. Yield 94% of theory; boiling point = 87°–90° C./0.04 mbar; $n_D^{25} = 1.5011$; fragrance note: herbal, spicy.

EXAMPLE 3

43 g (0.5 mole) of 3-methyl-but-3-en-1-ol and 71 g (0.5 mole) of ethyl 3-formyl-crotonate were dissolved in 200 ml of toluene, 0.3 g of p-toluenesulfonic acid was added to the solution and the mixture was refluxed for 1.5 hours, during which 9 ml of water were distilled off azeotropically. The reaction mixture was then washed neutral with water, the solvent was removed at 30° C./10 mbar, and the residue was subjected to fractional distillation. This gave 70 g of a main fraction (63% of theory), which according to the NMR spectrum contained about 70% of 2-(1-methyl-2-carbethoxy-eth-1-en-1-yl)-4-methylene-tetrahydropyran, about 20% of 2-(1-methyl-2-carbethoxy-eth-1-en-1-yl)-4-methyl-5,6-dihydro-2H-pyran and about 10% of 2-(1-methyl-2-carbethoxy-eth-1-en-1-yl)-4-methyl-2,3-dihydro-6H-pyran; boiling point 92°–95° C./0.15 mbar; $n_D^{25} = 1.4878$; fragrance note: green, fruity.

EXAMPLE 4

86 g (1 mole) of 3-methyl-but-3-en-1-ol and 118.5 g (1 mole) of 2-methyl-4-chloro-but-2-en-1-al were dissolved in 300 ml of toluene, 0.5 g of p-toluenesulfonic acid was added to the solution and the mixture was refluxed for 3 hours, during which 18 ml of water were distilled off azeotropically.

The reaction mixture was then washed neutral with sodium bicarbonate solution, the toluene was distilled off at 30° C. and 10 mbar and the residue was subjected to fractional distillation. This gave 131 g of a main fraction (70% of theory), which according to the NMR spectrum contained about 60% of 2-(1-methyl-3-chloro-prop-1-en-1-yl)-4-methylene-tetrahydropyran, about 30% of 2-(1-methyl-3-chloro-prop-b 1-en-1-yl)-4-methyl-5,6-dihydro-2H-pyran and about 10% of 2-(1-methyl-3-chloro-prop-1-en-1-yl)-4-methyl-2,3-dihydro-6H-pyran; boiling point 56°–64° C./1 mbar; $n_D^{25} = 1.5010$; fragrance note; spicy, aromatic, green.

EXAMPLE 5

86 g (1 mole) of 3-methyl-but-3-en-1-ol and 143 g (0.78 mole) of 77 percent strength 3-methyl-4-acetoxy-but-2-en-1-al were dissolved in 1.4 liters of toluene, 1.4 g of p-toluenesulfonic acid were added to the solution and the mixture was refluxed for 1 hour, during which 19 ml of water were distilled off azeotropically. The reaction mixture was then washed neutral with dilute sodium hydroxide solution, the toluene was distilled off at 30° C. and 10 mbar and the residue was subjected to fractional distillation. 103 g of a main fraction (63% of theory) were obtained. According to the NMR spectrum and gas-chromatographic analysis, the isomer composition was as follows: 56% of 2-(2-methyl-3-acetoxy-prop-1-en-1-yl)-4-methylenetetrahydropyran, 21% of 2-(2-methyl-3-acetoxy-prop-1-en-1-yl)-4-methyl-5,6-dihydro-2H-pyran and 23% of 2-(2-methyl-3-acetoxy-prop-1-en-1-yl)-4-methyl-2,3-dihydro-6H-pyran; boiling point 75°–81° C./0.1 mbar; $n_D^{25} = 1.4776$; fragrance note: citrus-like, slightly floral.

EXAMPLE 6

86 g (1 mole) of 3-methyl-but-3-en-1-ol and 128 g (1 mole) of 4-acetoxy-but-3-en-1-al were dissolved in 250 ml of toluene, 0.5 g of p-toluenesulfonic acid was added to the solution and the mixture was refluxed for 3 hours, during which 19 ml of water distilled off azeotropically. The reaction mixture was then washed neutral with dilute sodium hydroxide solution, the toluene was distilled off at 30° C. and 10 mbar and the residue was subjected to fractional distillation. This gave 112.5 g of a main fraction (62% of theory). According to the NMR spectrum, in conjunction with gas-chromatographic analysis, the isomer composition was as follows: about 65% of 2-(3-acetoxy-prop-1-en-1-yl)-4-methylene-tetrahydropyran, about 30% of 2-(3-acetoxy-prop-1-en-1-yl)-4-methyl-5,6-dihydro-2H-pyran and about 5% of 2-(3-acetoxy-prop-1-en-1-yl)-4-methyl-2,3-dihydro-6H-pyran; boiling point 78°–80° C./0.1 mbar; $n_D{}^{25}=1.4778$; fragrance note: floral, sweetish, fresh, bergamot-like.

We claim:
1. 2,4-Disubstituted pyran derivatives of the general formula I

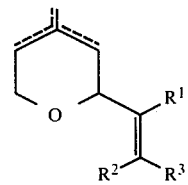

(I)

where $R^1$ and $R^2$ are each hydrogen or methyl and $R^3$ is is —CH$_2$OH, —CH$_2$—O—COCH$_3$, —CH$_2$—OCHO, —CH$_2$—O—COC$_2$H$_5$, —COOCH$_3$, —COOC$_2$H$_5$, —COOC$_3$H$_7$, —CH$_2$Cl, —CH$_2$Br, —CH$_2$I or —CHO, and which possess a double bond within the region shown by the broken line.

* * * * *